United States Patent [19]
Paulin et al.

[11] Patent Number: 5,914,395
[45] Date of Patent: Jun. 22, 1999

[54] DESMIN ENHANCER SEQUENCES, VECTORS COMPRISING THESE SEQUENCES AND THEIR USES IN COMPOSITIONS FOR THE EXPRESSION OF NUCLEOTIDE SEQUENCES IN TRANSFECTED CELLS

[75] Inventors: Denise Paulin, Vincennes, France; Zhen Lin Li, Paris, France

[73] Assignees: Institut Pasteur, Paris Cedex, France; Universite Paris 7, Paris Cedex, France

[21] Appl. No.: 08/894,228

[22] PCT Filed: Feb. 16, 1996

[86] PCT No.: PCT/FR96/00261

§ 371 Date: Sep. 12, 1997

§ 102(e) Date: Sep. 12, 1997

[87] PCT Pub. No.: WO96/26284

PCT Pub. Date: Aug. 29, 1996

[30] Foreign Application Priority Data

Feb. 20, 1995 [FR] France .................................. 95 01937

[51] Int. Cl.[6] .......................... C07H 21/04; C07H 21/02; C12P 21/00; C12Q 1/68
[52] U.S. Cl. ............................. 536/24.1; 435/6; 435/69.1; 435/240.2; 435/320.1; 435/172.3; 536/23.1; 536/24.3; 536/24.31; 536/24.33
[58] Field of Search .................................. 536/23.1, 24.1, 536/24.2, 24.31, 24.32, 24.37, 24.5; 435/6, 320.1, 91.2, 172.3, 69.5, 240, 252.3

[56] References Cited

U.S. PATENT DOCUMENTS

4,983,518   1/1991   Schaffner et al. ..................... 435/69.1

OTHER PUBLICATIONS

Li et al., "Different factors interact with myoblast specific and myotube specific enhcaner regions of the human desmin gene", J. Biol. Chem. 268 (14):10403–10415, May, 1993.

Harris et al., "Strategies for targeted gene therapy", Trends Genetics 12(10):400–405, 1996.

Marshall, "Gene Therapy's growing pains",Science 269:1050–1055, Aug. 1995.

*Primary Examiner*—Jeffrey Fredman
*Attorney, Agent, or Firm*—Oblon, Spivak, McClelland, Maier & Neustadt, P.C.

[57] ABSTRACT

The invention teaches modified desmin enhancer sequences which yield high level expression of operably linked DNA sequences. The claimed modified desmin enhancer sequences may be operably linked to genes encoding a protein. Further these modified desmin enhancer sequences may be placed into vectors including plasmids and transformed into cells including bacteria or myoblasts. Finally, these modified desmin enhancers may be used in methods of expression of proteins in the transformed bacteria or myoblasts.

67 Claims, 2 Drawing Sheets

FIG. 1

```
         MEF2                    MT            MyoD1                                                                          CAT
                                                                                                                           ACTIVITY
3   AAGCTTCTCC CTATAAATACC CGCTC GGTATTT GGGGT GCAGCTGT GCTGCCAGGGAGATGGTTGGGTTGACTCTAGA   100
4   AAGCTTCTCCTCGAGAAATACCCGCTCTGGTATTTGGGGTTGGCAGCTGTGCTGCCAGGGAGATGGTTGGGTTGACTCTAGA      8
5   AAGCTTCTCCTCTAGGCCTACCCGCTCTGGTATTTGGGGTTGGCAGCTGTGCTGCCAGGGAGATGGTTGGGTTGACTCTAGA     28
6   AAGCTTCTCCTCTATAAATAGGAGCTCTGGTATTTGGGGTTGGCAGCTGTGCTGCCAGGGAGATGGTTGGGTTGACTCTAGA    120
7   AAGCTTCTCCTCTATAAATACCCGCGGGTATTTGGGGTTGGCAGCTGTGCTGCCAGGGAGATGGTTGGGTTGACTCTAGA      130
8   AAGCTTCTCCTCTATAAATACCCGCTCTGAGATCTGGGGTTGGCAGCTGTGCTGCCAGGGAGATGGTTGGGTTGACTCTAGA     27
9   AAGCTTCTCCTCTATAAATACCCGCTCTGGTATCCGGGGTTGGCAGCTGTGCTGCCAGGGAGATGGTTGGGTTGACTCTAGA     41
10  AAGCTTCTCCTCTATAAATACCCGCTCTGGATCCGGGGTTGGCAGCTGTGCTGCCAGGGAGATGGTTGGGTTGACTCTAGA      15
11  AAGCTTCTCCTCTATAAATACCCGCTCTGGTATTTAAAGTTGGCAGCTGTGCTGCCAGGGAGATGGTTGGGTTGACTCTAGA    108
12  AAGCTTCTCCTCTATAAATACCCGCTCTGGTATTTGGGGTTGGAATCTGTTGCTGCCAGGGAGATGGTTGGGTTGACTCTAGA     3
13  AAGCTTCTCCTCGAGAAATACCCGCTCTGGATCCGGGGTTGGCAGCTGTGCTGCCAGGGAGATGGTTGGGTTGACTCTAGA       5
14  AAGCTTCTCCTCTAGGCCTACCCGCTCTGGATCCGGGGTTGGCAGCTGTGCTGCCAGGGAGATGGTTGGGTTGACTCTAGA      15
```

DESMIN ENHANCER SEQUENCES, VECTORS COMPRISING THESE SEQUENCES AND THEIR USES IN COMPOSITIONS FOR THE EXPRESSION OF NUCLEOTIDE SEQUENCES IN TRANSFECTED CELLS

BACKGROUND OF THE INVENTION

1. Field of the Invention

The present invention relates to amplifying sequences and vectors comprising these sequences, to the use of these vectors in compositions for the expression of nucleotide sequences in these transfected cells, and to the use of these products for therapeutic and vaccine applications.

2. Description of the Background

The desmine gene, one of the first muscle proteins to be detected in the developing embryo of mammals, was sequenced in 1989 by Li et al. (Gene, 78,243–254).

Subsequently, an amplifying sequence of 280 base pairs, situated between the nucleotides −693 and −973 upstream from the transcription initiation site, was described (Li and Paulin, 1991, J.Biol.Chem., 266 6562–6570).

This amplifying sequence was identified by producing a series of plasmid constructions carrying the bacterial gene coding for chloramphenicol acetyl transferase (CAT), and by introducing them into myogenic or non-myogenic mice cells. The authors show that this amplifying region of 280 base pairs can activate both homologous and heterologous promoters regardless of their orientation, position or distance in relation to this sequence.

The study of this sequence was continued (Li et al., 1993, J.Biol.Chem., 268, 10 403–10.415) and showed that this sequence contained two regions: one active in myotubes and the other active in myoblasts.

The part that is active in myotubes lies between positions −973 and −848, that is to say in a sequence of 125 nucleotides.

Within this sequence, a region lying between positions −910 and −870 is protected from the action of a DNase. This region contains binding sites of MEF2 and MyoD1 factors. No specific activity is indicated for this region of 40 nucleotides. In particular, no experiment has been carried out with constructions containing this isolated region. Mention has only been made that MyoD1 and MEF2 sites are necessary to obtain full amplifying activity in the myotubes.

The amplifying effect of the sequence upstream from the desmine gene has also been tested in a transgenic mouse (Li et al., 1993, Development, 117,947–959). A fragment of 1 kb containing the regulatory sequence upstream from the desmine gene is bound to a reporting gene coding for *Escherichia coli* β-galactosidase. The authors show that the amplifying activity of the desmine promoter is very considerable as the activity of β-galactosidase can be easily detected in tissue sections.

It arises from the prior art analysed above, that the amplifying properties of certain parts upstream from the human desmine gene are known. On the other hand, the regions responsible for this amplifying activity have not been identified.

They could therefore not be successfully modified with a view to improving their performance for the expression of genes or nucleotide sequences corresponding in whole or in part to these c-DNAs (complementary DNAs) coding for proteins of interest or for fragments of these proteins conveying epitopes able to induce protective antibodies or antibodies which recognise said epitopes. The preferable length of c-DNA or genomic DNA fragments is between 30 base pairs and 2 kb. They can be produced by chemical synthesis or by restriction enzyme cutting of DNA extracted from cells or micro-organisms selected by methods known to men of the art.

It is known that by introducing DNA into these eucaryote cells using the described methods, in particular by patent WO-90 11 092, it is not possible to obtain an extended or a high quality expression of said DNAs introduced in plasmid form.

SUMMARY OF THE INVENTION

The present invention brings an improvement in the expression level of genetic material introduced into transfected cells by means of constructions which use all or part of the activating sequences identified for the desmine gene and which can be used for the expression of any other gene or genetic material (genomic DNA fragments, c-DNA fragments etc..) in muscle tissue.

In particular, it is possible to use said sequences to express nucleotide sequences having an immunomodulatory function, such as cytokines, or immunogenic properties, such as the VPI protein of the polio virus or HBs protein of the hepatitis-B virus.

Another application lies in the area of gene therapy. In particular and in general, techniques which require the introduction of DNA into tissues necessitate the use of nucleotide sequences or vectors containing such, or liposomes strongly expressing the genes or cDNAs carried by these sequences. To date, this problem has not been solved in satisfactory manner.

The applicant therefore sought to determine which parts of the desmine gene regulatory sequences were responsible for the amplifying activity.

DETAILED DESCRIPTION OF THE INVENTION

Figure 2:
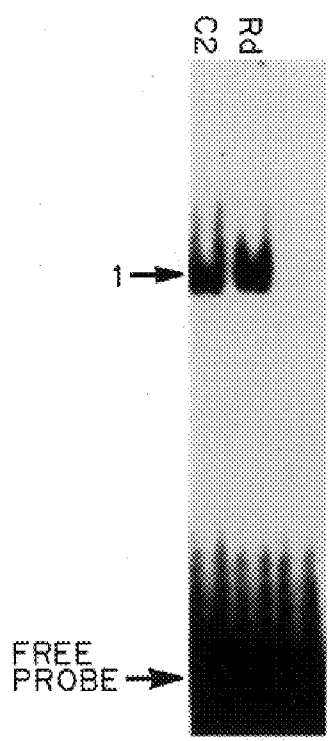

In surprising manner the applicant identified the role played by a sequence lying between the MEF2 and MyoD1 sites in the amplifying activity.

He also found that by coupling such amplifying sequence to a promoter, it is possible to obtain the expression of genes or cDNAs coding for peptides, polypeptides or proteins of therapeutic interest through the direct introduction of the DNA.

The object of the present invention is an amplifying sequence showing at least 90% homology with the following SEQ ID N° 1 sequence:

TCTATAAATA $X_1X_2X_3$GC $Y_1Y_1Y_1$GG TATTTGGGGT TGGCAGCTGT T (SEQ ID NO: 1) in which:

$X_1$, $X_2$ and $X_3$ may independently represent respectively C or G, C or G, and C or A.

$Y_1$, $Y_2$ and $Y_3$ may independently represent respectively T or C, C or G, and T or C.

Such sequence can advantageously hybridize under stringent conditions with the sequence SEQ ID N° 1.

Such conditions are for example the following:

Hybridization at 65° C. overnight: buffer:

0.2% polyvinyl pyrrolidone 0.2% ficoli 400

0.2% bovine serum albumin (BVS)

2×SSC

100 μg/ml salmon sperm DNA

100 μg/ml yeast RNA

Washings:

2×SSC 10 minutes at 65° C. once

2×SSC 30 minutes at 55° C. 4 times.

Another object of the present invention is an amplifying sequence showing at least 90% homology with the following SEQ ID N° 2 sequence (SEQ ID NO: 2):

ZGGTATT in which Z may be T or C.

Such sequence advantageously hybridizes under stringent conditions with sequence SEQ ID N° 2.

It will be noted that the present invention covers all amplifying sequences differing in one or several nucleotides in relation to sequences SEQ ID N° 1 or SEQ ID N° 2 whose functioning is not appreciably altered as well as their complementary sequences.

Under the present application, by amplifying sequence is meant a sequence which very strongly amplifies the transcription of one or more gene situated in cis.

The sequences of the invention include also sequence N° 3 or sequence N° 6, or sequence N° 7 or sequence N° 11, as defined with reference to the FIG. 1, either alone, in the form of polymers with two or eight identical fragments or in association with one of the four sequences.

The term "vector" is used to designate a nucleic acid molecule into which it is possible to insert fragments of foreign nucleic acid, for subsequent introduction into and maintaining within a host cell.

By "liposome" is meant any lipid composition able to fix RNA or DNA in covalent or non-covalent manner.

The present invention also relates to a sequence or an expression vector comprising said sequence and at least:

a sequence of type SEQ ID N° 1 pr SEQ ID N° 2 such as described above, in one or more copies, with the exception of sequences in which $X_1, X_2, X_3$ and $Y_2$ represent a cytosine (C), and $Y_1$ and $Y_3$ represent a thymidine (T) or Z represents (T), in which case the sequences SEQ ID N° 1 or SEQ ID N° 2 are at least two copies thereof, and a sequence coding for a protein or corresponding to the genomic sequence coding for said protein or part thereof.

Advantageously, such sequence, or said vector is completed by one or more promoter(s) enabling the expression of said protein in cells transfected by said DNA.

The protein may be at least part of a bacterial antigen, for example H. pylori urease, so-called HSP (A) an abbreviation for "Heat-shock protein A", or the HSP (B) protein, or of a viral antigen, for example the surface antigen of the hepatitis virus, in particular hepatitis-B, and preferably the HBs protein in one of its S forms, S-preS2 or S-preS2-preS1. It may also be a protein of a hepatitis-A virus, or of a non-A, non-B hepatitis virus such as hepatitis C, E or delta.

The sequences of the genes or proteins of the bacteria or viruses of these hepatites are described or can be deduced from the following documents: patent FR-79 21 811 (published under N° 2 464 269); FR-30 09 039 (published under N° 2 480 779), EP-81 400 634 (published under N° 0 038 765), FR-84 03 564 (published under N° 2 560 890), EP-91 830 479 (published under N° 0 485 347) and FR-88 13 135 (publication N° 2 637 612), PCT application published under N° WC 94/26 901 and article by Najarian et al. (Proc. Natl. Acad. Sci. USA, 1985, 82, 2627–2631).

The protein may also be a protein or part of a protein of the HIV-1 virus or the HIV-2 virus or the HTLV-1 virus, in particular the ENV protein (corresponding to the viral envelope) or the gag protein. The sequence of the part of the protein or peptide is chosen in relation to the function it is wished to express. The minimal nucleotide sequences lie advantageously between 20 and 50 base pairs.

In respect of the HTLV-1 virus, the proteins or sequences coding for these proteins may be those described in the following documents, or may be deduced from these documents: applications PCT/WO 93/05 843, PCT/WO 90 15 820, EP-O 352 060 and EP-O 269 445, and articles by Gray et al. (1990, Virology, 177, 391–395), Tanaka et al. (1991, J.Immunol., 147,354–360) and Nakamura et al. (1987, Int. J. Cancer, 40,403–407).

Generally, said protein may be one or more proteins of therapeutic or vaccine interest, such as proteins of interest for immunotherapy, for example the Interleukins, the growth factors, for example fibroblast growth factors (FGF) or the nerve growth factor (NGF) or the maltase gene, proteins able to induce an immune response, whether humoral, cytotoxic or cell immunity, or proteins which allow complementary gene activity in a gene normally expressed in the individual to be treated but which is no longer expressed either through mutation or deletion of its sequence.

Said protein may be a hybrid protein, made up for example of at least one part of the desmine and at least one part of a protein whose deficiency it is sought to counterbalance. In this case, the sequence or the vector may comprise an activating or amplifying sequence of the desmine gene, a sequence coding for at least one part of the desmine and a sequence coding for the protein whose deficiency it is sought to counterbalance.

It will be noted that the amplifying sequences may be positioned indifferently either upstream or downstream from the sequence coding for a protein, or a fragment thereof, or for a peptide lying between 10 and 50 aminoacids, and its promoter, and may lie in the two possible orientations.

In addition to a sequence coding for a protein or a fragment thereof, and an amplifying sequence, said sequence or vector may also comprise other regulatory sequences of Krox type, such as the Krox 24 sequence (LEMAIRE,P. et al. 1990, Mol. Cell.Biol., 10, 3456–3467).

The promoter may be any promoter either alone or in association with another promoter allowing the expression of the protein as defined above. It may therefore be a promoter internal to the gene to be expressed or to the cDNA coding for the protein or fragment thereof to be expressed. It may also be a promoter that is homologous to the host, such as the promoter of a gene in a protein of the cytoskeleton, in particular that of desmine as described by BOLMONT et al. (Journal of submicroscopic cytology and pathology, 1990, 22, 117–122) or LI et al. (Gene, 1989, 78, 243–254).

It may also be a heterologous promoter, such as that of a virus, for example that of thymidine kinase in the herpes virus (HSV).

In addition to the promoter, positioned upstream from the sequence coding for the protein or any fragment thereof, the sequence may also comprise a terminal transcription sequence positioned downstream from the sequence coding for the protein.

Finally, such sequence, or such vector, may comprise sequences allowing homologous recombination in the treated organism, specific to the gene to be replaced, said sequences being positioned upstream and downstream from the sequence coding for a protein, and possibly from the natural activating sequences and/or from the promoter or promoters. Owing to the presence of such sequences, the undesired gene existing in the treated organism will be replaced by the gene carried by the vector or the sequence, and which it is sought to have expressed in the organism.

Said homologous recombination method may be of the type described by Le Mouellic et al. (1990, Proc. Natl. Acad. Sci. USA, 87, 4712–4716) or in application PCT WO 91/05 667.

A vector such as defined above may also comprise a replicating origin that is active in a micro-organism, such as a bacterium.

Said vector may also comprise a gene allowing its selection in said micro-organism, such as an antibiotic resistant gene. It may be a plasmid.

Advantageously, such micro-organism is *Escherichia coli*.

The expression vectors containing the sequences to be expressed and the transfectable sequences, that are the subject of the present invention, may be obtained by methods known to men of the art, in particular by chemical synthesis, such as the method marketed by Applied Biosystem, or using genetic engineering methods. Such methods are those described in particular by Maniatis T. et al. 1982—Molecular Cloning, A Laboratory Manual, Cold Spring Harbor—Ed. New York, or one of its recent re-editions.

The invention also relates to two plasmids whose identification references are respectively EO3D CAT and DMT tk CAT (see Examples 1 and 2 below), which were filed with the CNCM collection of Institut Pasteur on Dec. 16th 1994 under registration numbers I-1508 and I-1509 respectively.

A further object of the present invention is a pharmaceutical composition comprising a pharmacologically effective quantity of one of the expression vectors or of one of the nucleotide sequences comprising at least one of the activating sequences of the invention described above which can be expressed without a vector in the cells to be transfected.

Such composition may also comprise pharmaceutically compatible excipients.

The present invention also relates to a medicinal product or vaccine containing these sequences and vectors.

Although this invention is not limited to a specific treatment, the vectors and sequences are preferably intended for use with a vaccine purpose, and particular for injection into muscle tissues. For this method of use of the invention the chosen promoter is advantageously that of a gene or a cDNA coding for a muscle protein or fragment thereof.

The present invention is illustrated but not limited by the following examples.

The FIG. 1 illustrates the mutation effect in the amplifying sequence of the DMT tk CAT vector on the activity of the gene coding for the CAT it carries (SEQ ID NO: 3–14).

The FIG. 2 is an autoradiogram of a gel of nuclear extracts of cellular lines C 2,7 (well C2) and CCL 136 (well Rd) incubated with labelled MT oligonucleotide. The position of the MT-protein complex is indicated by the number 1.

Figure 3:
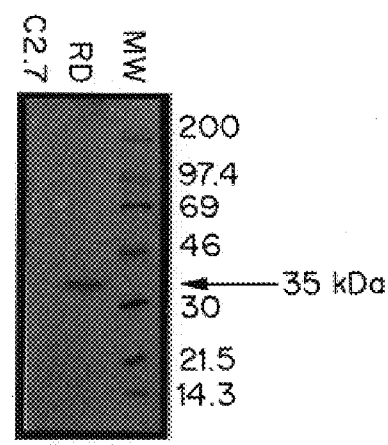

The FIG. 3 is an autoradiogram of a filter obtained by Southwestern blotting of cellular extra acts of cellular lines C 2,7 and CCL 136 with labelled MT oligonucleotide. Molecular weight markers (Sigma) have been migrated in well MW.

EXAMPLE 1

Preparation of the expression vector D MT k CAT Using two primers (1) DesHindIII
5'-GAAAGCTTCTCCTCTATAAATACC-3' (SEQ ID NO: 15) or (2) DesXbaI
5'-CCTCTAGAGTCAACCCAACCTCT-3' (SEQ ID NO: 16 a fragment of 84 base pairs containing a fixation site (GGCAGCTGTT) (SEQ ID NO: 17) for the MyoD1 transactivator factor, a fixation site (CTATAAATACC) (SEQ ID NO: 18) for the MEF2 factor and a site (GGTATTT) (SEQ ID NO: 19) called MT was amplified from the promoter of the human desmine gene. This 84 bp fragment was inserted into the HindIII-XbaI restriction sites of the pBLCAT2 plasmid (Lucknow and Schütz, 1987, Nucl.Acid. Res., 15,5490) which contains the basal promoter of the thymidine kinase gene of the herpes simplex virus and the region encoding the bacterial gene chloramphenicol acetyltransferase (CAT).

Owing to the co-operation between the MT site and sites MyoDI and MEF2, this fragment of 84 bp increases the expression of the CAT indicator gene 60 times in the differentiated muscle cells, the myotubes.

EXAMPLE 2

Preparation of the expression vector EO3 D CAT

A fragment of 280 base pairs (−973 to −693) containing the amplifier of the human desmine gene was placed before the 228 bp region (Li and Paulin 1991,1993, previously quoted) which contains the basal promoter of the human desmine gene and the region coding for the bacterial gene chloramphenicol acetyltransferase (CAT).

A fragment of 280 base pairs (−973 to −693) containing the amplifier of the human desmine gene was tailed by the polymerase DNA (Klenow) and inserted into the Hind III restriction site which was also free-ended with the polymerase DNA (Klenow).

This amplifier not only operates in differentiated muscle cells, but also in mononucleated muscle cells, the myoblasts, This fragment activates the expression of the gene in the myotubes 100 times and in the myoblasts 10 times.

EXAMPLE 3

Mutation effects in the amplifying region of the desmine gene on the activity of a reporting gene in the myotubes The DMT tk CAT vector whose preparation was described in Example 1, was mutated using the guided mutagenasis method (Kunkel et al. 1985, PNAS,82,p.488–492). These mutated vectors were transfected in culture myoblasts and the CAT activity was evidenced in the manner described by Li et al. (1991 and 1993 previously quoted).

The results of these experiments are summarized in the FIG. 1. Eleven constructions numbered from 4 to 14 showing various underlined mutations were tested for their effect on CAT activity. The non-muted amplifying sequence is the one represented at position 3.

It is very clearly apparent that the mutations of constructions 6 and 7 give rise to overamplification of CAT activity in relation to construction N° 3.

The two expression vectors in Examples 1 and 2 may be used to construct vectors for the expression of the gene of therapeutic interest in muscle cells through replacing the CAT gene by the chosen gene. The EcoRI and BamH I sites may be used to remove the CAT gene.

The CAT gene may therefore be replaced for the immunisation or vaccination of mammals with bare DNA or genomic DNA corresponding to the genes coding for the envelope and gag protein of the HTLVI virus (Cary et al., 1990; Virology 177, 391–395; Tanaka et al., 1991, J. Immunology 147; 354–360; Nakamura et al. 1987; Int. J. Cancer 40: 403–407); the gene coding for all or part of the envelope of the hepatitis B virus or of human papillomae such as HPV16, HPV33 etc..; the gene coding for the FIV envelope, or for gene therapy, the genes coding for the interleukins and growth factors (FGF, NGF, MG-CSF etc. . . . ) and for gene therapy of myopathy due to maltase deficiency.

EXAMPLE 4

Identification of a protein which specifically binds the MT sequence (GGTATTT)

Materials and methods

1. Method of gel delay.

Nuclear extracts obtained from muscular cell lines C 2,7 (Li and Paulin, 1991, J. Biol. Chem., 266, 6562–6570) and Rhabdomyosarcoma (accessible to ATCC under N° CCL 136) are incubated with radiolabelled oligonucleotide MT, at room temperature during 10 minutes. The reaction mixtures are then resolved in 5% acrylamide gel. After 3 hours migration, the gel is dried and autoradiographed.

The mixtures have been performed in 20 µl, and contain 750 ng of sonicated salmon sperm DNA, 3 µg of nuclear extract, 15 mM HEPES pH 8, 0.1 mM EDTA, 1 mM DTT, 2 mM $MgCl_2$, 70 mM NaCl, 15% glycerol.

2) Southwestern blotting

Nuclear extracts are prepared from muscular cell lines C 2,7 and Rhabdomyosarcoma. 40 µg of proteines are resolved on a 10% SDS-PAGE gel. The proteins are then transferred on a nitrocellulose filter. The filter is incubated during 1 hour at 37° C. in a solution containing 5% of skimmed milk, 50 mM Tris pH 7,5; 50 mM NaCl; 0,1 mM EDTA, 1 mM DTT and then in a buffer containing the labelled probe MT. The filter is washed three times in the same buffer and autoradiographed.

Results

The gel-delay experimentations (FIG. 2) show that the MT sequence (GGTATTT) specifically binds a nuclear factor from murin (C 2,7) and human (Rhabdomyosarcoma) muscular cell lines.

The autoradiogram obtained by Southwestern blotting (FIG. 3) shows that the nuclear factor which binds the MT sequence is a 35 kDa protein.

This protein is found in the muscular cells such as C 2,7 and Rhabdomyosarcoma cells.

The quantity of this protein increases during the muscular differenciation.

---

We claim:

1. A single or double stranded enhancer DNA sequence comprising the following nucleotide sequence:

5'-TCTATAAATAX$_1$X$_2$X$_3$GCY$_1$Y$_2$Y$_3$GGTATTTGGGG-TTGGCAGCTGTT-3' (SEQ ID NO: 1) wherein $X_1$ is G,
$X_2$ is C or G,
$X_3$ is C or A,
$Y_1$ is T or C,
$Y_2$ is C or G, and
$Y_3$ is T or C.

2. A single or double stranded enhancer DNA sequence comprising the following nucleotide sequence:

5'-TCTATAAATAX$_1$X$_2$X$_3$GCY$_1$Y$_2$Y$_3$GGTATTTGGGG-TTGGCAGCTGTT-3' (SEQ ID NO: 1) wherein $X_1$ is C or G,
$X_2$ is G,
$X_3$ is C or A, $Y_1$ is T or C,
$Y_2$ is C or G, and
$Y_3$ is T or C.

3. A single or double stranded enhancer DNA sequence comprising the following nucleotide sequence:

5'-TCTATAAATAX$_1$X$_2$X$_3$GCY$_1$Y$_2$Y$_3$GGTATTTGGGG-TTGGCAGCTGTT-3' (SEQ ID NO: 1) wherein $X_1$ is C or G,
$X_2$ is C or G,
$X_3$ is A,
$Y_1$ is T or C,
$Y_2$ is C or G, and
$Y_3$ is T or C.

4. A single or double stranded enhancer DNA sequence comprising the following nucleotide sequence:

5'-TCTATAAATAX$_1$X$_2$X$_3$GCY$_1$Y$_2$Y$_3$GGTATTTGGGG-TTGGCAGCTGTT-3' (SEQ ID NO: 1) wherein $X_1$ is C or G,
$X_2$ is C or G,
$X_3$ is C or A,
$Y_1$ is C,
$Y_2$ is C or G, and
$Y_3$ is T or C.

5. A single or double stranded enhancer DNA sequence comprising the following (SEQ ID NO: 1) nucleotide sequence:

5'-TCTATAAATAX$_1$X$_2$X$_3$GCY$_1$Y$_2$Y$_3$GGTATTTGGGG-TTGGCAGCTGTT-3' wherein $X_1$ is C or G,
$X_2$ is C or G,
$X_3$ is C or A,
$Y_1$ is T or C,
$Y_2$ is G, and
$Y_3$ is T or C.

6. A single or double stranded enhancer DNA sequence comprising the following nucleotide sequence:

5'-TCTATAAATAX$_1$X$_2$X$_3$GCY$_1$Y$_2$Y$_3$GGTATTTGGGG-TTGGCAGCTGTT-3' (SEQ ID NO: 1) wherein $X_1$ is C or G,
$X_2$ is C or G,
$X_3$ is C or A,
$Y_1$ is T or C,
$Y_2$ is C or G, and
$Y_3$ is C.

7. A DNA sequence comprising the enhancer of claim 1 operably linked to a gene encoding a protein.

8. A DNA sequence comprising the enhancer of claim 2 operably linked to a gene encoding a protein.

9. A DNA sequence comprising the enhancer of claim 3 operably linked to a gene encoding a protein.

10. A DNA sequence comprising the enhancer of claim 4 operably linked to a gene encoding a protein.

11. A DNA sequence comprising the enhancer of claim 5 operably linked to a gene encoding a protein.

12. A DNA sequence comprising the enhancer of claim 6 operably linked to a gene encoding a protein.

13. The DNA sequence of claim 7, wherein the gene encodes a bacterial antigen, a viral antigen, an HIV-1 protein, a portion of an HIV-1 protein, an interleukin, a fibroblast growth factor, a nerve growth factor, a protein which is capable of inducing an immune, humoral or cytotoxic response, or a protein which allow complementary gene activity in a gene normally expressed in an individual to be treated.

14. The DNA sequence of claim 8, wherein the gene encodes a bacterial antigen, a viral antigen, an HIV-1 protein, a portion of an HIV-1 protein, an interleukin, a fibroblast growth factor, a nerve growth factor, a protein which is capable of inducing an immune, humoral or cytotoxic response, or a protein which allow complementary gene activity in a gene normally expressed in an individual to be treated.

15. The DNA sequence of claim 9, wherein the gene encodes a bacterial antigen, a viral antigen, an HIV-1 protein, a portion of an HIV-1 protein, an interleukin, a fibroblast growth factor, a nerve growth factor, a protein which is capable of inducing an immune, humoral or cytotoxic response, or a protein which allow complementary gene activity in a gene normally expressed in an individual to be treated.

16. The DNA sequence of claim 10, wherein the gene encodes a bacterial antigen, a viral antigen, an HIV-1 protein, a portion of an HIV-1 protein, an interleukin, a fibroblast growth factor, a nerve growth factor, a protein which is capable of inducing an immune, humoral or cytotoxic response, or a protein which allow complementary gene activity in a gene normally expressed in an individual to be treated.

17. The DNA sequence of claim 11, wherein the gene encodes a bacterial antigen, a viral antigen, an HIV-1 protein, a portion of an HIV-1 protein, an interleukin, a fibroblast growth factor, a nerve growth factor, a protein which is capable of inducing an immune, humoral or cytotoxic response, or a protein which allow complementary gene activity in a gene normally expressed in an individual to be treated.

18. The DNA sequence of claim 12, wherein the gene encodes a bacterial antigen, a viral antigen, an HIV-1 protein, a portion of an HIV-1 protein, an interleukin, a fibroblast growth factor, a nerve growth factor, a protein which is capable of inducing an immune, humoral or cytotoxic response, or a protein which allow complementary gene activity in a gene normally expressed in an individual to be treated.

19. A vector comprising the DNA sequence of claim 7.
20. A vector comprising the DNA sequence of claim 8.
21. A vector comprising the DNA sequence of claim 9.
22. A vector comprising the DNA sequence of claim 10.
23. A vector comprising the DNA sequence of claim 11.
24. A vector comprising the DNA sequence of claim 12.
25. The vector of claim 19, which is a plasmid.
26. The vector of claim 20, which is a plasmid.
27. The vector of claim 21, which is a plasmid.
28. The vector of claim 22, which is a plasmid.
29. The vector of claim 23, which is a plasmid.
30. The vector of claim 24, which is a plasmid.
31. A microorganism transformed with the vector of claim 19.
32. A microorganism transformed with the vector of claim 20.
33. A microorganism transformed with the vector of claim 21.
34. A microorganism transformed with the vector of claim 22.
35. A microorganism transformed with the vector of claim 23.
36. A microorganism transformed with the vector of claim 24.

37. The microorganism of claim 31, which is *Escherichia coli.*

38. The microorganism of claim 32, which is *Escherichia coli.*

39. The microorganism of claim 33, which is *Escherichia coli.*

40. The microorganism of claim 34, which is *Escherichia coli.*

41. The microorganism of claim 35, which is *Escherichia coli.*

42. The microorganism of claim 36, which is *Escherichia coli.*

43. A muscle cell transformed with the vector of claim 19.

44. A muscle cell transformed with the vector of claim 20.

45. A muscle cell transformed with the vector of claim 21.

46. A muscle cell transformed with the vector of claim 22.

47. A muscle cell transformed with the vector of claim 23.

48. A muscle cell transformed with the vector of claim 24.

49. The muscle cell of claim 43, which is a myoblast or a myotube.

50. The muscle cell of claim 44, which is a myoblast or a myotube.

51. The muscle cell of claim 45, which is a myoblast or a myotube.

52. The muscle cell of claim 46, which is a myoblast or a myotube.

53. The muscle cell of claim 47, which is a myoblast or a myotube.

54. The muscle cell of claim 48, which is a myoblast or a myotube.

55. A method of expressing a protein, comprising culturing the transformed microorganism of claim 31, wherein said protein encoded by said gene is expressed.

56. A method of expressing a protein, comprising culturing the transformed microorganism of claim 32, wherein said protein encoded by said gene is expressed.

57. A method of expressing a protein, comprising culturing the transformed microorganism of claim 33, wherein said protein encoded by said gene is expressed.

58. A method of expressing a protein, comprising culturing the transformed microorganism of claim 34, wherein said protein encoded by said gene is expressed.

59. A method of expressing a protein, comprising culturing the transformed microorganism of claim 35, wherein said protein encoded by said gene is expressed.

60. A method of expressing a protein, comprising culturing the transformed microorganism of claim 36, wherein said protein encoded by said gene is expressed.

61. A method of expressing a protein, comprising culturing the transformed muscle cell of claim 43, wherein said protein encoded by said gene is expressed.

62. A method of expressing a protein, comprising culturing the transformed muscle cell of claim 44, wherein said protein encoded by said gene is expressed.

63. A method of expressing a protein, comprising culturing the transformed muscle cell of claim 45, wherein said protein encoded by said gene is expressed.

64. A method of expressing a protein, comprising culturing the transformed muscle cell of claim 46, wherein said protein encoded by said gene is expressed.

65. A method of expressing a protein, comprising culturing the transformed muscle cell of claim 47, wherein said protein encoded by said gene is expressed.

66. A method of expressing a protein, comprising culturing the transformed muscle cell of claim 48, wherein said protein encoded by said gene is expressed.

67. A single or double stranded enhancer DNA sequence consisting of the following nucleotide sequence:

5'-TCTATAAATA$X_1X_2X_3$GC$Y_1Y_2Y_3$GGTATTTGGGG-TTGGCAGCTGTT-3' (SEQ ID NO: 1) wherein $X_1$ is C or G, $X_2$ is C or G, $X_3$ is C or A, $Y_1$ is T or C, $Y_2$ is C or G, and $Y_3$ is T or C.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 41 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (vi) ORIGINAL SOURCE:
      (A) ORGANISM: Homo sapiens (ix) FEATURE:
      (A) NAME/KEY: allele
      (B) LOCATION: replace(11, "g")

(ix) FEATURE:
      (A) NAME/KEY: allele
      (B) LOCATION: replace(12, "g")

(ix) FEATURE:
      (A) NAME/KEY: allele
      (B) LOCATION: replace(13, "a")

(ix) FEATURE:
      (A) NAME/KEY: allele
      (B) LOCATION: replace(16, "c")

(ix) FEATURE:
      (A) NAME/KEY: allele
      (B) LOCATION: replace(17, "g")

(ix) FEATURE:
      (A) NAME/KEY: allele
      (B) LOCATION: replace(18, "c")

(xi) SEQUENCE DESCRIPTION: SEQ ID NO:1:

TCTATAAATA CCCGCTCTGG TATTTGGGGT TGGCAGCTGT T                41

(2) INFORMATION FOR SEQ ID NO:2:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Homo sapiens (ix) FEATURE:
        (A) NAME/KEY: allele
        (B) LOCATION: replace(1, "c")

(xi) SEQUENCE DESCRIPTION: SEQ ID NO:2:

TGGTATTT                8

(2) INFORMATION FOR SEQ ID NO:3:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

AAGCTTCTCC TCTATAAATA CCCGCTCTGG TATTTGGGGT TGGCAGCTGT TGCTGCCAGG    60

GAGATGGTTG GGTTGACTCT AGA                83

(2) INFORMATION FOR SEQ ID NO:4:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

AAGCTTCTCC TCGAGAAATA CCCGCTCTGG TATTTGGGGT TGGCAGCTGT TGCTGCCAGG    60

GAGATGGTTG GGTTGACTCT AGA                83

(2) INFORMATION FOR SEQ ID NO:5:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

AAGCTTCTCC TCTAGGCCTA CCCGCTCTGG TATTTGGGGT TGGCAGCTGT TGCTGCCAGG    60

GAGATGGTTG GGTTGACTCT AGA                83

(2) INFORMATION FOR SEQ ID NO:6:

(i) SEQUENCE CHARACTERISTICS:
    (A) LENGTH: 83 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:6:

AAGCTTCTCC TCTATAAATA GGAGCTCTGG TATTTGGGGT TGGCAGCTGT TGCTGCCAGG    60

GAGATGGTTG GGTTGACTCT AGA    83

(2) INFORMATION FOR SEQ ID NO:7:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

AAGCTTCTCC TCTATAAATA CCCGCCGCGG TATTTGGGGT TGGCAGCTGT TGCTGCCAGG    60

GAGATGGTTG GGTTGACTCT AGA    83

(2) INFORMATION FOR SEQ ID NO:8:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

AAGCTTCTCC TCTATAAATA CCCGCTCTGA GATCTGGGGT TGGCAGCTGT TGCTGCCAGG    60

GAGATGGTTG GGTTGACTCT AGA    83

(2) INFORMATION FOR SEQ ID NO:9:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

AAGCTTCTCC TCTATAAATA CCCGCTCTGG TATCCGGGGT TGGCAGCTGT TGCTGCCAGG    60

GAGATGGTTG GGTTGACTCT AGA    83

(2) INFORMATION FOR SEQ ID NO:10:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

AAGCTTCTCC TCTATAAATA CCCGCTCTGG GATCCGGGGT TGGCAGCTGT TGCTGCCAGG    60

GAGATGGTTG GGTTGACTCT AGA                                              83

(2) INFORMATION FOR SEQ ID NO:11:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

AAGCTTCTCC TCTATAAATA CCCGCTCTGG TATTTAAAGT TGGCAGCTGT TGCTGCCAGG       60

GAGATGGTTG GGTTGACTCT AGA                                              83

(2) INFORMATION FOR SEQ ID NO:12:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

AAGCTTCTCC TCTATAAATA CCCGCTCTGG TATTTGGGGT TGGAATCTGT TGCTGCCAGG       60

GAGATGGTTG GGTTGACTCT AGA                                              83

(2) INFORMATION FOR SEQ ID NO:13:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

AAGCTTCTCC TCGAGAAATA CCCGCTCTGG GATCCGGGGT TGGCAGCTGT TGCTGCCAGG       60

GAGATGGTTG GGTTGACTCT AGA                                              83

(2) INFORMATION FOR SEQ ID NO:14:

(i) SEQUENCE CHARACTERISTICS:
        (A) LENGTH: 83 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

AAGCTTCTCC TCTAGGCCTA CCCGCTCTGG GATCCGGGGT TGGCAGCTGT TGCTGCCAGG       60

GAGATGGTTG GGTTGACTCT AGA                                              83

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear -continued (ii) MOLECULE TYPE: other nucleic acid
         (A) DESCRIPTION: /desc = "PRIMER"

(xi) SEQUENCE DESCRIPTION: SEQ ID NO:15:

GAAAGCTTCT CCTCTATAAA TACC                                24

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

CCTCTAGAGT CAACCCAACC TCT                                 23

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

GGCAGCTGTT                                                10

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

CTATAAATAC C                                              11

(2) INFORMATION FOR SEQ ID NO:19:

(i) SEQUENCE CHARACTERISTICS:
        (A) LENGTH: 7 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

GGTATTT                                                   7